United States Patent
Al-Hajjar

(10) Patent No.: US 7,176,206 B2
(45) Date of Patent: Feb. 13, 2007

(54) ANTIBIOTICS

(75) Inventor: Farouk Hussni Al-Hajjar, Amman (JO)

(73) Assignee: Dar Al Dawa Development and Investment Co. (JO)

( * ) Notice: Subject to any disclaimer, the term of this patent is extended or adjusted under 35 U.S.C. 154(b) by 0 days.

(21) Appl. No.: 10/473,039

(22) PCT Filed: Mar. 20, 2002

(86) PCT No.: PCT/IB02/00843

§ 371 (c)(1),
(2), (4) Date: Feb. 2, 2004

(87) PCT Pub. No.: WO02/079164

PCT Pub. Date: Oct. 10, 2002

(65) Prior Publication Data

US 2004/0132740 A1    Jul. 8, 2004

(30) Foreign Application Priority Data

Mar. 30, 2001    (EP) .................... 01107713

(51) Int. Cl.
*A61K 31/496* (2006.01)
*C07D 401/04* (2006.01)

(52) U.S. Cl. .......... 514/253.06; 514/253.07; 514/253.08; 544/363

(58) Field of Classification Search ......... 544/363; 514/253.06, 253.07, 253.08
See application file for complete search history.

(56) References Cited

U.S. PATENT DOCUMENTS

| 4,971,970 A | 11/1990 | Miyamoto et al. |
| 5,145,853 A | 9/1992 | Metzger et al. |
| 5,281,662 A | 1/1994 | Ito et al. |

FOREIGN PATENT DOCUMENTS

| DE | 35 25 108 | 12/1986 |
| DE | 36 08 745 | 1/1989 |
| EP | 93/18084 | * 8/1993 |
| ES | 2 006 098 | 4/1989 |
| ES | 2 006 099 | 4/1989 |
| WO | WO 93/07154 | 4/1993 |

OTHER PUBLICATIONS

Saugier, J. H. et al, "A facile synthesis of triethyl ortho (14 C) formate and its application to the preparation of a (2-14C) quinoline-3-carboxylic acid" Chemical Abstracts, vol. 106, No. 23, Jun. 8, 1987, XP 002178799.

* cited by examiner

*Primary Examiner*—Emily Bernhardt
(74) *Attorney, Agent, or Firm*—Fitch, Even, Tabin & Flannery

(57) ABSTRACT

The invention provides compounds of the general formula:

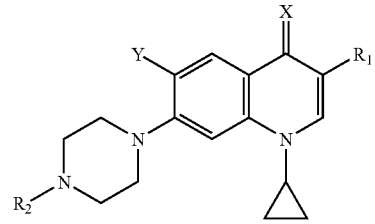

wherein
X is selected from the group consisting of oxygen, sulfur and nitrogen-containing groups selected from azine, oxime, hydrazone, aromatic hydrazone, aliphatic hydrazone, semicarbazone, guanidinyl group, and aliphatic or aromatic imines;
Y is selected from the group of halogens;
$R_1$ and $R_2$ are independently selected from the group consisting of H, lower alkyl group (of $C_1$ up to $C_6$), lower hydroxyalkyl group (of $C_1$ up to $C_6$), lower O-alkyl group (of $C_1$ up to $C_6$), lower alkylcarbonyl group (of $C_2$ up to $C_6$), lower alkyloxycarbonyl group (of $C_1$ up to $C_6$), haloalkylcarbonyl group (of $C_1$ up to $C_6$), or arylsulfonyl group, and their pharmaceutically acceptable salts.

The compounds are useful as active ingredients in pharmaceutical compositions. The invention relates to the use of the said compounds as a medicament, in particular as an antibiotic.

17 Claims, No Drawings

ANTIBIOTICS

The present application is directed to a new class of compounds which are useful active ingredients in pharmaceutical compositions, in particular as antibiotics.

Although a large variety of antibiotics, i.e. antibacterial agents, are available in the prior art, there is a continuous need for the development of new substances with this activity, in particular as many bacteria have developed resistances against known antibiotics.

From the prior art, ciprofloxacin (1-cyclopropyl-6-fluoro-1,4-dihydro-4-oxo-7-(1-piperazinyl)-3-quinolinecarboxylic acid) is known to be an effective antibacterial agent acting as a gyrase inhibitor. Other derivatives of 4-quinolinone-3-carboxylic acid, such as norfloxacin and ofloxacin, are also known to be active as antibiotics. For example, DE 35 25 108 A1 discloses a number of antibacterially active quinolone carboxylic esters.

M. Reuman, M. A. Eissenstat and J. D. Weaver III "Cyanide Mediated Decarboxylation of 1-Substituted-4-oxoquinoline and 4-oxo-1,8-naphthyridine-3-carboxylic Acids", Tetrahedron Letters, Vol. 35, No. 45, pp. 8303–8306 (1994) discloses the decarboxylation of 4-oxo-3-quinolinecarboxylic acids. However, no specific pharmaceutical activity is disclosed for such decarboxylated compounds.

H. Kondo, F. Sakamoto, K. Kawakami and G. Tsukamoto "Studies on Prodrugs. 7. Synthesis and Antimicrobial Activity of 3-Formylquinolone Derivatives", J. Med. Chem. 1988, 31, pp. 221–225 discloses 3-formyl quinolone derivatives.

WO 93/15084 is directed to novel cephalosporin compounds, disclosing, as intermediates of the synthesis thereof, specific quinolone derivatives.

Surprisingly, it has now been found that a group of compounds being structurally related to this known group of compounds such as ciprofloxacin and the like, but without the carboxylic acid or ester functionality, common to all such known active substances, are not only also highly effective as antibiotics, but even show a superior antibacterial effect.

Thus, this invention is related to a new class of compounds having the general formula (I)

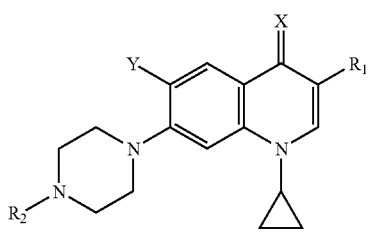

wherein

X is selected from the group consisting of oxygen, sulfur and nitrogen-containing groups selected from azine, oxime, hydrazone, aromatic hydrazone, aliphatic hydrazone, semicarbazone, guanidinyl group, or aliphatic or aromatic imines;

Y is selected from the group of halogens;

$R_1$ and $R_2$ are independently selected from the group consisting of H, lower alkyl group (of $C_1$ up to $C_6$), lower hydroxyalkyl group (of $C_1$ up to $C_6$), lower O-alkyl group (of $C_1$ up to $C_6$), lower alkylcarbonyl group (of $C_2$ up to $C_6$), lower alkyloxycarbonyl group (of $C_1$ up to $C_6$), haloalkylcarbonyl group (of $C_1$ up to $C_6$), or arylsulfonyl group, and their pharmaceutically acceptable salts, with the exception of a compound according to formula (I) with X being sulfur, $R_1$ being hydrogen and $R_2$ being either hydrogen or methyl, and a compound according to formula (I) with X being O, $R_1$ being hydrogen, and $R_2$ being hydrogen or ethyl.

A preferred group are the fluoroquinolinones, i.e. with X being oxygen and Y being fluorine. The presently most preferred compound is 1-cyclopropyl-6-fluoro-1,4-dihydro-4-oxo-7(1-piperazinyl)-quinoline, referred to as compound (A).

Suitable salts of the compounds according to formula (I) are those of inorganic and organic acids, e.g. hydrochloric acid, sulphuric acid, phosphoric acid, citric acid, malic acid, stearic acid, succinic acid, lactic acid, aspartic acid, glutamic acid, gluconic acid, acetic acid, and formic acid as examples; other acids are understood to be suitable as well.

The present invention is also related to a pharmaceutical composition comprising a compound having the general formula (I)

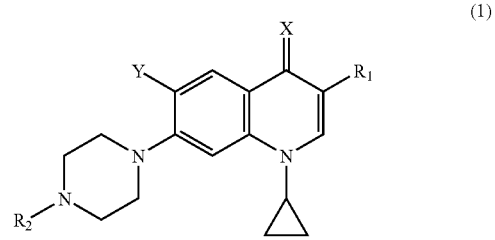

wherein

X is selected from the group consisting of oxygen, sulfur and nitrogen-containing groups selected from azine, oxime, hydrazone, aromatic hydrazone, aliphatic hydrazone, semicarbazone, guanidinyl group, or aliphatic or aromatic imines;

Y is selected from the group of halogens;

$R_1$ and $R_2$ are independently selected from the group consisting of H, lower alkyl group (of $C_1$ up to $C_6$), lower hydroxyalkyl group (of $C_1$ up to $C_6$), lower O-alkyl group (of $C_1$ up to $C_6$), lower alkylcarbonyl group (of $C_2$ up to $C_6$), lower alkyloxycarbonyl group (of $C_1$ up to $C_6$), haloalkylcarbonyl group (of $C_1$ up to $C_6$), or arylsulfonyl group, or a pharmaceutically acceptable salt thereof, as active ingredient together with pharmaceutically acceptable adjuvants, diluents, excepients or carriers, in all known pharmaceutical dosage forms.

Furthermore, the present invention is related to a compound having the general formula (I)

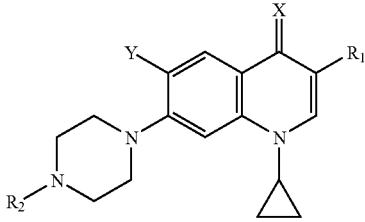

(1)

wherein
X is selected from the group consisting of oxygen, sulfur and nitrogen-containing groups selected from azine, oxime, hydrazone, aromatic hydrazone, aliphatic hydrazone, semicarbazone, guanidinyl group, or aliphatic or aromatic imines;
Y is selected from the group of halogens;
$R_1$ and $R_2$ are independently selected from the group consisting of H, lower alkyl group (of $C_1$ up to $C_6$), lower hydroxyalkyl group (of $C_1$ up to $C_6$), lower O-alkyl group (of $C_1$ up to $C_6$), lower alkylcarbonyl group (of $C_2$ up to $C_6$), lower alkyloxycarbonyl group (of $C_1$ up to $C_6$), haloalkylcarbonyl group (of $C_1$ up to $C_6$), or arylsulfonyl group, or a pharmaceutically acceptable salt thereof or the composition according to claim 6 for use as a medicament for the treatment of humans and animals.

Finally, the invention is directed to the use of a compound having the general formula (I)

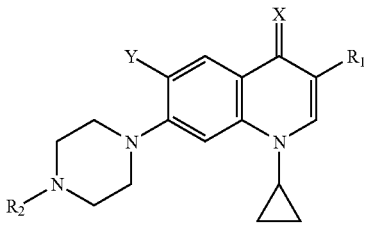

(1)

wherein
X is selected from the group consisting of oxygen, sulfur and nitrogen-containing groups selected from azine, oxime, hydrazone, aromatic hydrazone, aliphatic hydrazone, semicarbazone, guanidinyl group, or aliphatic or aromatic imines;
Y is selected from the group of halogens;
$R_1$ and $R_2$ are independently selected from the group consisting of H, lower alkyl group (of $C_1$ up to $C_6$), lower hydroxyalkyl group (of $C_1$ up to $C_6$), lower O-alkyl group (of $C_1$ up to $C_6$), lower alkylcarbonyl group (of $C_2$ up to $C_6$), lower alkyloxycarbonyl group (of $C_1$ up to $C_6$), haloalkylcarbonyl group (of $C_1$ up to $C_6$), or arylsulfonyl group, or a pharmaceutically acceptable salt thereof or of a composition according to claim 6 as an antibiotic.

Experimental Procedure:

The initial starting material used in this invention for the preparation of all the example compounds according to formula (I) specified in the Examples is ciprofloxacin (where $R_1$=COOH; $R_2$=H; Y=F; X=O). Compound (A) is prepared from ciprofloxacin as follows:

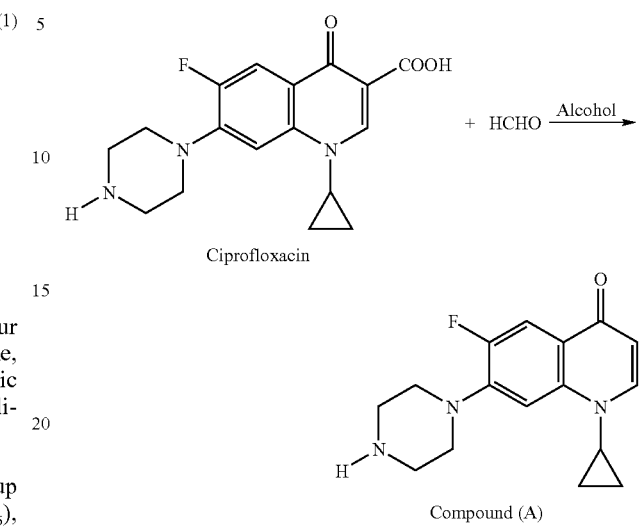

Ciprofloxacin

Compound (A)

A mixture of ciprofloxacin (5.0 g) and formaldehyde solution (25 ml) in n-butanol (50 ml) was refluxed for 3 hours. The solvent was evaporated. The precipitated solid was crystallized from methanol or ethanol as colourless leaflet crystals to give 1-cyclopropyl-6-fluoro-1,4-dihydro-4-oyo-7(1-piperazinyl)-quinoline, referred to as compound (A) in this invention. It has a m.p. of 188–190°, with a yield of 4.1 g, representing 94.5% percent yield from the starting materials. Compound (A) could be prepared under the same experimental conditions using other alcohols with a lower alkyl group from $C_1$ to $C_5$.

The hydrochloride salt of this compound was prepared by stirring (5.0 g) of compound (A) in ethanol (15 ml) and the pH of the solution was adjusted to pH 2.7–3.2 using hydrochloric acid solution. The precipitated white product was separated by filtration, dried at 65° C. It has a m.p. with decomposition at 321–323°. Compound (A) was confirmed using several spectroscopic techniques as follows:

IR (KBr, $cm^{-1}$): 1257, 1471, 1500, 1629, 1757; MS: $M^+$(287), ($M^+$-$C_2H_4N$), ($M^+$-$C_3H_7N$), ($M^+$-$C_4H_9N$); NMR:

The salts of the preferred embodiment of the invention compound (A) were prepared by digesting compound (A) with alcohol of lower alkyl group from $C_1$ to $C_3$. The pH of the solution is adjusted to pH between 2.0–5.0 with maximum yield at pH of 2.8–3.0 with the relevantly used acid to adjust the pH. The resulting salt may contain varying amount of water, which can be adjusted to be one mole of water in the resulting salt by drying the salt at a temperature ranging from 60–70° C.

The hydrochloride salt of the said compound (A) is stable and more soluble in water than ciprofloxacin hydrochloride. It gave a better antibacterial effect towards gram-positive and gram-negative organisms than ciprofloxacin hydrochloride when both compounds are tested under the same experimental conditions.

Another preferred embodiment of the invention is 1-cyclopropyl-6-fluoro-7-methylpiperazino-4-oxo-1,4-dihydroquinoline will be referred to as Compound (B) of this invention, which is formed in good yield by reacting compound (A) with aliphatic aldehydes of lower alkyl group of $C_1$ to $C_6$. The hydrochloride salt of Compound (B) was obtained in then same method used for compound (A) salt preparation. Compound (B) hydrochloride salt gave better antibacterial effect towards gram-positive and gram-negative organisms than ciprofloxacin hydrochloride. Other derivatives from compound (A) were also prepared as shown in the examples of this invention.

The following examples are cited to explain the invention but not to limit the scope of the invention in any way.

EXAMPLE 1

1-cyclopropyl-6-fluoro-1,4-dihydro-4-oxo-7-(1-(4-methyl)piperazinyl)-quinoline

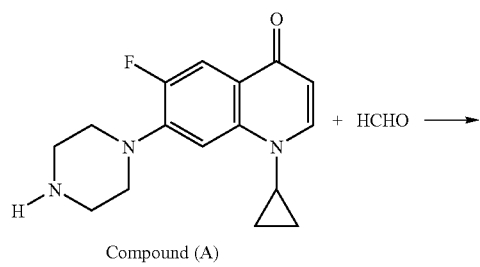 + HCHO ⟶

Compound (A)

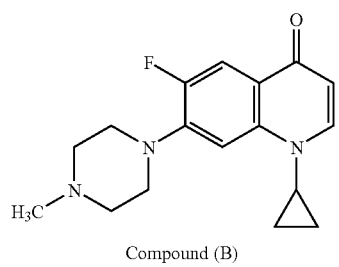

Compound (B)

5.0 g of compound (A) was refluxed with 20 ml formaldehyde solution for 3 hours. The separated solid was crystallized from ethanol to give the corresponding 1-cyclopropyl-6-fluoro-1,4-dihydro-4-oxo-7-(1-(4-methyl) piperazinyl)-quinoline, referred to as compound (B), in yield of 4.5 g as colourless crystals. It has m.p. 238–240°. The hydrochloride salt of compound (B) was prepared by the same method used for the preparation of the hydrochloride salt of compound (A).

IR spectrum of salt B (KBr, cm$^{-1}$): 1271, 1471, 1643, 1743. MS: M$^+$ 301.

EXAMPLE 2

1-cyclopropyl-6-fluoro-1,4-dihydro-4-oxo-7-(1-(4-chloroacetyl)-piperazinyl)-quinoline

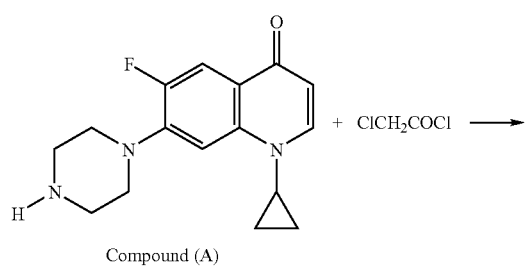 + ClCH$_2$COCl ⟶

Compound (A)

-continued

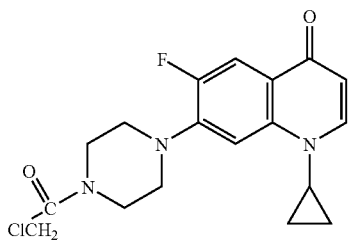

A solution of chloroacetyl chloride (2.5 ml) in acetone (10 ml) was added with stirring to a solution of 1-cyclopropyl-6-fluoro-1,4-dihydro-4-oxo-7-(1-piperazinyl)-quinoline (A) (5.0 g) in acetone (20 ml) containing pyridine (5 ml) during 15 min. The precipitated product was separated by filtration to give the corresponding 1-cyclopropyl-6-fluoro-1,4-dihydro-4-oxo-7-(1-(4-chloroacetyl)-piperazinyl)-quinoline as colourless crystals, m.p. 262–64°. Its hydrochloride salt has a melting point with decomposition at 309–310° C.

IR spectrum of salt (KBr, cm$^{-1}$): 1273, 1350, 1480, 1500, 1630, 1730.

EXAMPLE 3

1-cyclopropyl-6-fluoro-1,4-dihydro-4-oxo-7-(1-4-methoxycarbonyl)-piperazinyl)-quinoline

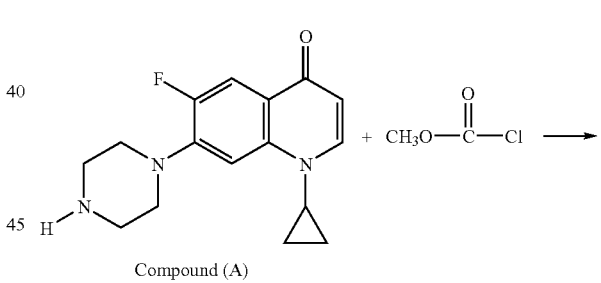

Compound (A)

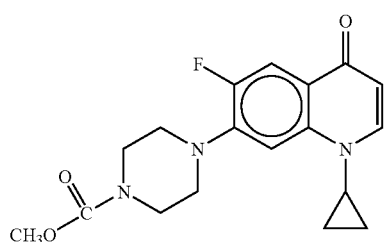

The title compound was synthesized from compound (A) by a procedure analogous to that method mentioned under example 2 using methyl chloroformate instead of chloroacetyl chloride. The product was separated as colourless crystals with m.p. 206–207° C.

IR spectrum (KBr, cm$^{-1}$): 1275, 1300, 1380, 1480, 1500, 1635, 1730, 1750.

EXAMPLE 4

1-cyclopropyl-6-fluoro-1,4-dihydro-4-hydrazono-7-(1-piperazinyl)-quinoline

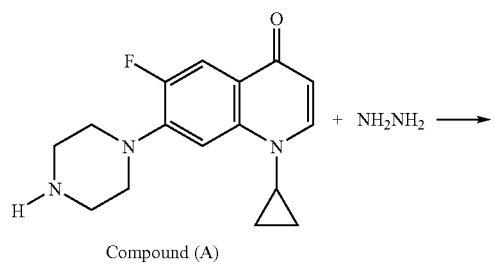

Compound (A)

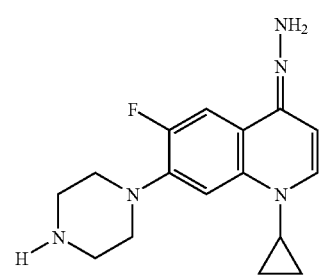

A mixture of 2.0 g of compound (A) and 4 ml hydrazine hydrate in 15 ml ethanol was refluxed on water-bath for 2 hours. The precipitated solid was separated by filtration. The product was re-crystallized from ethanol to give colourless crystals with m.p. 270–272° C.

IR spectrum (KBr, cm$^{-1}$): 1270, 1320, 1380, 1480, 1630, 3400 (broad); MS: 301(M$^+$)

EXAMPLE 5

1-cyclopropyl-6-fluoro-1,4-dihydro-4-guanidino-7-(1-piperazinyl)-quinoline

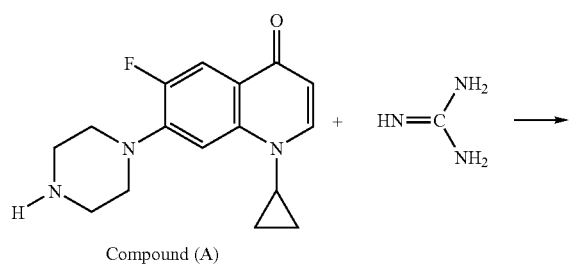

Compound (A)

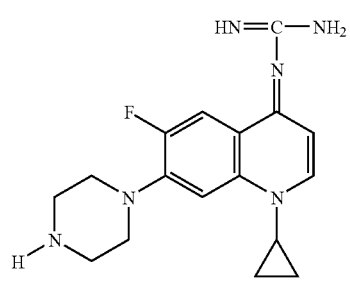

A solution of guanidine hydrochloride (1.5 g) in 10 ml water was added to a solution of compound (A) in ethanol (20 ml) containing (1.0 g) sodium carbonate. The mixture was refluxed for 3 hours. The precipitated solid was separated by filtration and had a m.p. 248–250° C.

IR spectrum (KBr, cm$^{-1}$): 1270, 1320, 1390, 1480, 1629, 3400 (broad)

EXAMPLE 6

1-cyclopropyl-6-fluoro-1,4-dihydro-4-oxo-7-(1-(4-p-tosyl)-piperazinyl)-quinoline

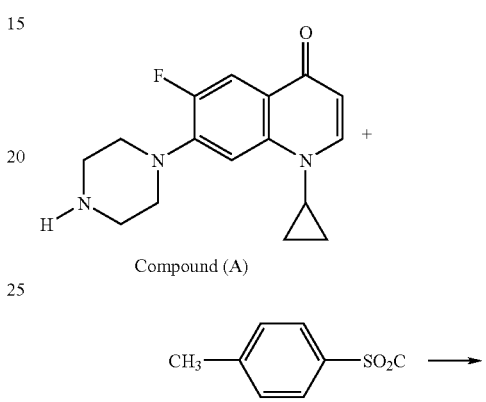

Compound (A)

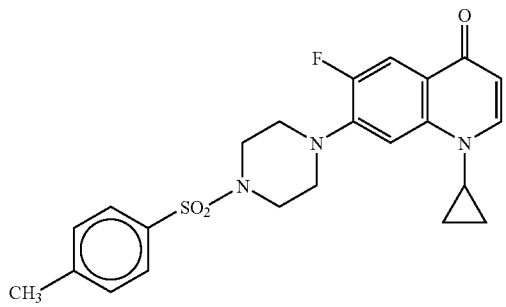

The title compound was prepared from compound (A) by a procedure similar to that method mentioned under example 2 using p-tolylsulfonyl chloride (p-tosyl chloride). The product was separated as pale yellow crystals with m.p. 264–266° C.

IR spectrum (KBr, cm$^{-1}$): 1270, 1350, 1475, 1495, 1510, 1630, 1730

Antimicrobial Activity of the Compounds of the Present Invention:

An aqueous solution of the salts of the compounds reported in this invention namely compound (A) and compound (B) were tested in vitro against *E. coli* and St. aureus according to an established clinical procedure (Mackie and McCartney: Practical Medical Microbiology, Churchill livingstone, 1996, 14$^{th}$ edition, p 159–163). The results show that these compounds gave better antibacterial effect against gram-positive and gram-negative organisms than ciprofloxacin-HCl as a reference compound. Table (1) below shows the minimum inhibitory concentrations (MIC) of compound (A) compared to ciprofloxacin in their hydrochloride salt.

TABLE 1

Minimum Inhibitory Concentration (MIC)

| Tested compound | E. coli | St. aureus |
|---|---|---|
| Ciprofloxacin HCl salt | 0.02 µg/ml | 0.15 µg/ml |
| Compound (A) HCl salt | 0.01 µg/ml | 0.08 µg/ml |

The minimum inhibitory concentration (MIC) of compound (A) and ciprofloxacin were also studied using clinically isolated microorganism *staphylococcus aureus* and *pseudomotias aeruginose*.

Table (2) reports the effective maintenance dose of the compounds of the invention necessary to control bacterial re-growth. The experimental work was carried out according to an established clinical procedure on mice (Mackie and McCartney, ibid). The results obtained show that compound (A) is more sensitive and effective as antibacterial agents than ciprofloxacin hydrochloride. This fact was elucidated after further incubation of the positive samples for up to 16 hours for both compounds in which, the results show that, growth rate of bacteria in the sample related to ciprofloxacin hydrochloride increased with time, while compound (A) showed very slow bacterial growth at a dose of 0.0 µg/ml. This reflects the ability of compound (A) to virtually inhibiting the growth of bacteria compared to ciprofloxacin under the same experimental conditions as stated in this text.

TABLE 2

| | Micro organism | |
|---|---|---|
| Material | *Staphylococcus aureus* | *Pseudomones aeruginose* |
| Ciprofloxacin HCl salt | 0.08 µg/ml | 0.06 µg/ml |
| Compound (A) HCl | 0.06 µg/ml | 0.05 µg/ml |

$LD_{50}$ for both compounds were also studied on mice according to an established clinical procedure (Mackie and McCartney, ibid) and the results are reported in table (3).

TABLE 3

$LD_{50}$ for the compounds of the invention

| Compound | $LD_{50}$ |
|---|---|
| Ciprofloxacin HCl salt | 8 mg/kg mice |
| Compound (A), HCl salt | 28 mg/kg mice |

The features disclosed in the foregoing description and in the claims may both separately and in any combination thereof, be material for realizing the invention in diverse forms thereof.

What is claimed is:

1. A compound having the formula (I)

(1)

wherein
X is oxygen, a hydrazone group, or a guanidinyl group;
Y is a halogen;
$R_1$ is selected from the group consisting of H, a $C_1$–$C_6$ alkyl group, a $C_1$–$C_6$ hydroxyalkyl group, a $C_1$–$C_6$ O-alkyl group, a $C_2$–$C_6$ alkylcarbonyl group, a $C_1$–$C_6$ haloalkylcarbonyl group, or an arylsulfonyl group; and
$R_2$ is selected from the group consisting of H, a $C_1$–$C_6$ alkyl group, a $C_1$–$C_6$ hydroxyalkyl group, a $C_1$–$C_6$ O-alkyl group, a $C_2$–$C_6$ alkylcarbonyl group, a $C_1$–$C_6$ alkyloxycarbonyl group, a $C_1$–$C_6$ haloalkylcarbonyl group, or an arylsulfonyl group;
or pharmaceutically acceptable salt thereof, with the proviso that the compound is other than a compound of formula (I) where X is O, $R_1$ is H, and $R_2$ is H or ethyl.

2. The compound according to of claim 1, wherein X is oxygen.

3. The compound according to of claim 1, wherein Y is fluorine.

4. The compound according to claim 1 wherein $R_1$ and $R_2$ are independently selected from H or a $C_1$–$C_6$ alkyl group.

5. The compound according to claim 4, wherein both $R_1$ and $R_2$ are H.

6. The compound 1-cyclopropyl-6-fluoro-7-methypiperazino4-oxo-1,4- dihydroquinoline or pharmaceutically acceptable salts thereof.

7. The compound 1-cyclopropyl-6-fluoro-1,4-dihydro-4-oxo-7-(1-(4-chloroacetyl)-piperazinyl)-quinoline or pharmaceutically acceptable salts thereof.

8. The compound 1-cyclopropyl-6-fluoro-1,4-dihydro-4-oxo-7-(1-(4-methoxycarbonyl)-piperazinyl)-quinoline or pharmaceutically acceptable salts thereof.

9. The compound 1-cyclopropyl-6-fluoro-1,4-dihydro-4-hydrazine-7-(1-piperazinyl)-quinoline or pharmaceutically acceptable salts thereof.

10. The compound 1-cyclopropyl-6-fluoro-1,4-dihydro-4-guanidino-7-(1-piperazinyl)-quinoline or pharmaceutically acceptable salts thereof.

11. A pharmaceutical composition comprising a compound of claim 1,
as active ingredient; and
a pharmaceutically acceptable adjuvant, diluent, excipient or carrier.

12. An antimicrobial composition which comprises an effective amount of:
1-cyclopropyl-6-fluoro-7-methypiperazino-4-oxo-1,4-dihydroquinoline,
1-cyclopropyl-6-fluoro-1,4-dihydro-4-oxo-7-(1-(4-chloroacetyl)-piperazinyl)-quinoline,
1-cyclopropyl-6-fluoro-1,4-dihydro-4-oxo-7-(1-(4-methoxycarbonyl)-piperazinyl)-quinoline,
1-cyclopropyl-6-fluoro-1,4-dihydro-4-hydrazine-7-(1-piperazinyl)-quinoline,
1-cyclopropyl-6-fluoro-1,4-dihydro-4-guanidino-7-(1-piperazinyl)-quinoline, or combinations thereof, and
a pharmaceutically acceptable adjuvant, diluent, excipient or carrier.

13. A method for treating bacterial infection in a subject comprising administering an antibacterially effective amount of a compound of the formula presented in claim 1.

14. A method for treating bacterial infection in a subject comprising administering an antibacterially effective amount of a pharmaceutical composition of claim 11.

15. A method for inhibiting bacterial growth comprising administering to the bacteria an effective around of a compound of the formula presented in claim 1.

16. The method of claim 15, wherein the bacterial growth is in vitro.

17. The method of claim 15, wherein the bacterial growth is in vivo.

* * * * *

UNITED STATES PATENT AND TRADEMARK OFFICE
CERTIFICATE OF CORRECTION

| | | |
|---|---|---|
| PATENT NO. | : 7,176,206 B2 | Page 1 of 1 |
| APPLICATION NO. | : 10/473039 | |
| DATED | : February 13, 2007 | |
| INVENTOR(S) | : Al-Hajjar | |

It is certified that error appears in the above-identified patent and that said Letters Patent is hereby corrected as shown below:

On the Title Page item 56:

Under Foreign Patent Documents: Delete "EP 93/18084 * 8/1993" and insert --EP 93/15084 * 8/1993--.

In the Claims:

Column 10, Line 14: After "or" insert --a--;

Column 10, Line 26 (approx.): Delete "azino4-oxo-1" and insert --azino-4-oxo-1--.

Signed and Sealed this

Third Day of July, 2007

JON W. DUDAS
*Director of the United States Patent and Trademark Office*